(12) United States Patent
Wakamatsu et al.

(10) Patent No.: US 7,763,019 B2
(45) Date of Patent: Jul. 27, 2010

(54) ELECTROSURGICAL INSTRUMENT

(75) Inventors: Mai Wakamatsu, Hino (JP); Tomoyuki Takashino, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 484 days.

(21) Appl. No.: 11/633,351

(22) Filed: Dec. 4, 2006

(65) Prior Publication Data

US 2008/0132889 A1    Jun. 5, 2008

(51) Int. Cl.
*A61B 18/14* (2006.01)
(52) U.S. Cl. ........................................ 606/49
(58) Field of Classification Search .............. 606/49
See application file for complete search history.

(56) References Cited

U.S. PATENT DOCUMENTS

| 5,167,659 A * | 12/1992 | Ohtomo et al. ............ 606/40 |
| 6,890,332 B2 * | 5/2005 | Truckai et al. ............ 606/41 |
| 2004/0116793 A1 | 6/2004 | Taimisto et al. |

FOREIGN PATENT DOCUMENTS

| EP | 0 546 767 A2 | 6/1993 |
| EP | 0 740 926 A2 | 11/1996 |
| JP | 7-34805 | 4/1995 |
| JP | 7-250811 | 10/1995 |
| JP | 3318733 | 6/2002 |
| JP | 2003-70914 | 3/2003 |
| WO | WO 03/047696 A1 | 6/2003 |
| WO | WO 03/075777 A1 | 9/2003 |
| WO | WO 2006/038645 A1 | 4/2006 |

OTHER PUBLICATIONS

Patent Abstracts of Japan—Japanese Publication No. 09-224951, published Sep. 2, 1997.
Patent Abstracts of Japan—Japanese Publication No. 04-022354, published Jan. 27, 1992.

* cited by examiner

*Primary Examiner*—Lee S Cohen
(74) *Attorney, Agent, or Firm*—Scully, Scott, Murphy & Presser, P.C.

(57) ABSTRACT

An electrosurgical instrument of the present invention includes an elongated instrument body, a cylindrical member constituting the instrument body, an ultrasonic transducer provided in inside of the cylindrical member for applying ultrasonic vibration to a fluid flowing into a liquid feed passage, a fluid atomizing port provided at the distal side of the instrument body for injecting the liquid which was given the ultrasonic vibration by the ultrasonic transducer and atomized to a living tissue from the distal end of the instrument body, and an electrode provided at the distal side of the instrument body for discharging high-frequency electric energy along the liquid injected from the fluid atomizing port so as to coagulate a surface layer of the living tissue.

2 Claims, 8 Drawing Sheets

ELECTROSURGICAL INSTRUMENT

BACKGROUND OF THE INVENTION

1. Field of the Invention

The present invention relates to an electrosurgical instrument using both high-frequency electric energy and a conductive fluid for coagulating a surface layer of a living tissue by electric discharge through the atomized conductive fluid.

2. Description of the Related Art

Recently, as an electrosurgical instrument using both high-frequency electric energy and a conductive fluid for coagulating a surface layer of a living tissue by electric discharge through the atomized conductive fluid, instruments such as a treatment instrument for an abdominal surgery, a treatment instrument used with a rigid endoscope, a flexible treatment instrument used with a flexible endoscope, and the like are known.

In Japanese Patent No. 3318733, for example, a surgical device is proposed for incision or coagulation of a living tissue by conducting a high-frequency electric current between a nozzle electrode and a portion to be treated through a conductive fluid jet injected from the nozzle electrode toward the portion to be treated.

Specifically, in the surgical device disclosed in Japanese patent No. 3318733, such a construction is provided that, after a discharge column is formed between the nozzle electrode and the portion to be treated, the fluid jet as a focusing flow is injected from the nozzle electrode toward the portion to be treated of a living tissue for incision/coagulation of the living tissue in a non-contact manner from the nozzle electrode using discharge current energy flowing to the portion to be treated through the fluid jet.

Moreover, Japanese Examined Patent Application Publication No. H07-034805 discloses a coagulating device for non-contact hemostatic coagulation of a living tissue from an active electrode by conducting a high-frequency current from the active electrode to the living tissue through the conductive fluid while atomizing the conductive fluid mixed with gas from a distal hole of the active electrode.

SUMMARY OF THE INVENTION

In brief, an electrosurgical instrument of the present invention comprises an elongated instrument body, a cylindrical member constituting the instrument body, an ultrasonic transducer provided in the inside of the cylindrical member for applying ultrasonic vibration to the conductive fluid flowing into the inside of the cylindrical member, a fluid atomizing port provided at the distal side of the instrument body for injecting the conductive fluid which was given the ultrasonic vibration by the ultrasonic transducer and atomized to a living tissue from the distal end of the instrument body, and an electrode provided at the distal side of the instrument body for discharging the high-frequency electric energy along the conductive fluid injected from the fluid atomizing port so as to coagulate surface layer of the living tissue.

The above and other objects, features and advantages of the invention will become more clearly understood from the following description referring to the accompanying drawings.

DESCRIPTION OF THE PREFERRED EMBODIMENTS

Prior to description of an embodiment of the present invention referring to the drawings, a problem of the present invention will be explained.

Recently, as an electrosurgical instrument using both high-frequency electric energy and a conductive fluid for coagulating a surface layer of a living tissue by discharge, instruments such as a treatment instrument for an abdominal surgery, a treatment instrument used with a rigid endoscope, a flexible treatment instrument used with a flexible endoscope and the like are known.

In Japanese Patent No. 3318733, for example, a surgical device is proposed for incision or coagulation of a living tissue by conducting a high-frequency electric current between a nozzle electrode and a portion to be treated through a conductive fluid jet injected from the nozzle electrode toward the portion to be treated of the living tissue.

Specifically, in the surgical device disclosed in Japanese patent No. 3318733, such a construction is provided that, after a discharge column is formed between the nozzle electrode and the portion to be treated, the fluid jet as a focusing flow is injected from the nozzle electrode toward the portion to be treated of a living tissue so as to pass through the discharge column for incision/coagulation of the living tissue in the non-contact manner from the nozzle electrode using discharge current energy flowing to the portion to be treated through the fluid jet.

Moreover, Japanese Examined Patent Application Publication No. H07-034805 discloses a coagulating device for non-contact hemostatic coagulation of a living tissue from an active electrode by conducting a high-frequency current from the active electrode to the living tissue through the conductive fluid while atomizing the conductive fluid mixed with gas from a distal hole of the active electrode.

Here, it is necessary to reduce an injection amount of a conductive fluid to be supplied to a living body in order to improve a coagulability for the living tissue.

However, in the construction of the invention described in Japanese Patent No. 3318733, the conductive fluid is injected from the nozzle electrode, but since there is limitation in reduction of a flow rate of the injected liquid in injection from the nozzle electrode, there is a problem that the coagulability for the target tissue is hard to be increased.

Also, it is necessary to reduce the dimension of an injection hole formed at the nozzle electrode as much as possible in order to reduce the injection amount from the nozzle electrode, but because of limitation in machining in actuality, it is difficult to machine the injection hole of the nozzle electrode to a required sufficiently reduced size.

Moreover, if the dimension of the injection hole of the nozzle electrode is reduced, it becomes necessary to raise feeding pressure of the liquid, which requires a separate high-pressure water feed device and increases manufacturing costs.

From the above, as a result, there is a problem in the construction of the invention described in Japanese Patent No. 3318733 in which a focusing flow is injected from the nozzle electrode that it is difficult to improve coagulability for the target tissue.

Also, in order to maintain sufficient coagulability for the target tissue, favorable discharge from the nozzle electrode is required. However, for the sufficient discharge, it is necessary to reduce a diameter of an atomized particle of the liquid injected from the nozzle electrode as much as possible, but in the invention described in Japanese Patent No. 3318733, there is also a problem that sufficient reduction of the atomized particle diameter is limited since the focusing flow is injected from the nozzle electrode.

Here, the invention described in Japanese Examined Patent Application Publication No. H07-034805, which is a method for atomizing a liquid from a distal hole of an active electrode by generating a mist at a mixing point between the supplied liquid and gas, has a construction capable of reducing the flow rate of the liquid by supply of the gas.

However, in the construction of the invention described in Japanese Examined Patent Application Publication No. H07-034805, there is a problem that reduction of the atomized particle diameter of the liquid is limited and as a result, sufficient discharge is hard to be generated and sufficient coagulability for the target tissue is difficult to be obtained.

In addition, since a gas supply pipeline and a device for feeding gas are needed separately from a liquid supply pipeline, there is a problem that a structure becomes complicated both as a coagulating device and a treatment instrument provided at the coagulating device.

The present invention was made in view of the above problems and its object is to provide an electrosurgical instrument using both high-frequency electric energy and a conductive fluid for coagulating a surface layer of a living tissue by electric discharge through the atomized conducted fluid, which can reduce an injection amount of the liquid to be injected to a target tissue and moreover improves coagulability for the target tissue by generating atomization of the liquid with a smaller particle diameter with a simple construction.

An embodiment of the present invention will be described below referring to the attached drawings. It should be noted that in the embodiments shown below, as an electrosurgical instrument using both the high-frequency electric energy and the conductive fluid for coagulating the surface layer of the living tissue by electric discharge, a medical treatment instrument is used as an example in description. Also, in the description below for the treatment instrument, the side to be inserted into a body cavity is referred to as the distal side and the operation portion side as the proximal side.

First Embodiment

Figure 1:
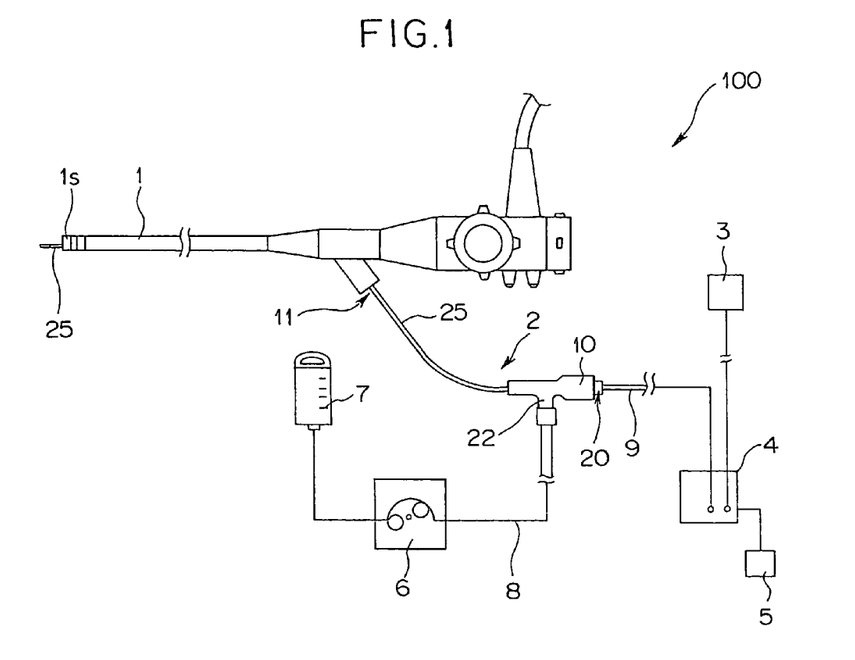
FIG. 1 is a block diagram showing a treatment instrument system provided with a treatment instrument showing a first embodiment.
Figure 2:
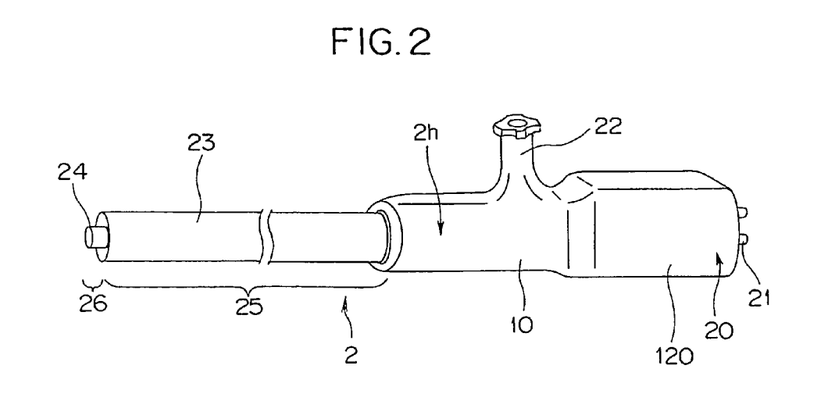
FIG. 2 is an enlarged perspective view of a treatment instrument in FIG. 1.
Figure 3:
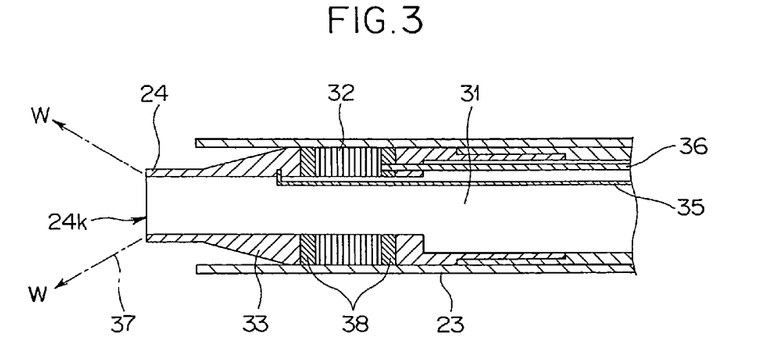
FIG. 3 is a partial sectional view of the distal side of the treatment instrument in FIG. 2.
Figure 4:
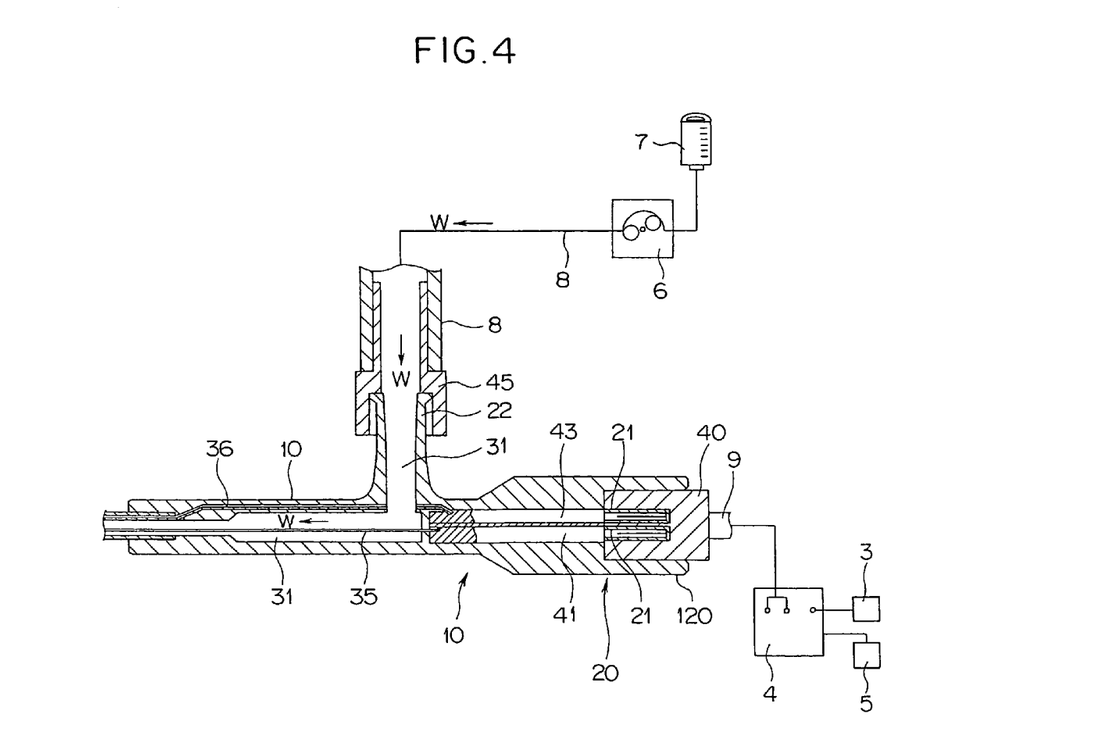
FIG. 4 is a partial sectional view of the proximal side of the treatment instrument in FIG. 2.

FIG. 1 is a block diagram showing a treatment instrument system provided with a treatment instrument showing this embodiment, FIG. 2 is an enlarged perspective view of the treatment instrument in FIG. 1, FIG. 3 is a partial sectional view of the distal side of the treatment instrument in FIG. 2, and FIG. 4 is a partial sectional view of the proximal side of the treatment instrument in FIG. 2.

As shown in FIG. 1, a treatment instrument system 100 mainly includes a treatment instrument 2 capable of insertion/withdrawal with respect to a treatment channel 11 of an endoscope 1, a high-frequency/ultrasonic driving power source (hereinafter abbreviated simply as a power source) 4, which is a power source which is connectable to the treatment instrument 2, and a liquid feed pump 6.

The treatment instrument 2 is provided with an elongated instrument body 2h (See FIG. 2), and the instrument body 2h mainly includes an insertion portion 25, which is an elongated cylindrical member, and a proximal portion 10, which is consecutively provided at the proximal side of the insertion portion 25 and is a cylindrical member.

At the proximal portion 10, a connector 22 for liquid feed tube, which is a liquid feed connector, and a cable connection portion 20 are provided.

To the connector 22 for liquid feed tube, one end of a liquid feed tube 8 with the liquid feed pump 6 interposed at the middle position is connected. Specifically, as shown in FIG. 4, a tube base 45 is provided at one end of the liquid feed tube 8, and this tube base 45 is connected to the connector 22 for liquid feed tube. By this, inside of the liquid feed tube 8 communicates with a liquid feed passage 31 inside the connector 22 for liquid feed tube.

Also, to the other end of the liquid feed tube 8, a liquid feed container 7, which is a liquid supply source in which a liquid for liquid feed, which is a conductive fluid, (hereinafter abbreviated simply as a liquid) W is reserved is connected. The liquid W is preferably an electrolytic solution such as normal saline solution, for example.

The connector 22 for liquid feed tube is to flow the liquid fed by the liquid feed pump 6 from the liquid feed container 7 through the liquid feed tube 8 into the liquid feed passage 31 inside the treatment instrument 2.

To the cable connection portion 20, the other end of a conductive cable 9 having one end connected to the power source 4 is connected. To the power source 4, a foot switch 5 for controlling output of the treatment instrument and a return electrode 3 stuck to the body surface of a subject are connected.

Also, at the cable connection portion 20, as shown in FIG. 2, a plug 21 to which the other end of the conductive cable 9 is connected and a plug cover 120 partially covering the periphery of the plug 21 are provided.

As shown in FIG. 4, a cable connector 40 is provided at the other end of the conductive cable 9, and by the cable connector 40, the other end of the conductive cable 9 and the plug 21 are connected to each other. By this, a high-frequency current, which is high-frequency electric energy, and a current for ultrasonic driving are transmitted to the treatment instrument 2 from the power source 4.

The insertion portion 25 is formed with a thickness capable of insertion/withdrawal with respect to the treatment channel 11 of the endoscope 1, and it is formed with a length sufficient to be projected from a distal portion 1s of the endoscope 1, when it is inserted into the treatment channel 11, 1 to 3 meters, for example.

Also, as shown in FIG. 2, the insertion portion 25 has a flexible elongated tube 23 constituting an outer surface of the insertion portion 25. Thus, the tube 23 is formed with a length suitable for use to be inserted into the treatment channel 11 of the endoscope 1 similarly to the insertion portion 25. Also, the tube 23 constitutes a cylindrical member in this embodiment.

Moreover, at the distal side of the instrument body 2h, that is, the distal side of the insertion portion 25 and inside of the tube 23, a tubular electrode 24 constituting a treatment portion 26 is disposed.

As shown in FIG. 3, a transducer 32 having hollow structure is disposed inside the tube 23, and at the distal side of the transducer 32, a tubular conical horn 33 for amplifying the amplitude of the transducer 32 is connected through an insulating plate 38, which will be described later.

The horn 33 has its distal end disposed inside the tube 23 so that its distal end protrudes to the distal side than the distal end of the tube 23. Also, at the distal end of the horn 33, the electrode 24 is constituted.

Moreover, to the horn 33, the other end of a high-frequency conductive line 35, which is a lead wire, having one end connected to the plug 21 is connected. The high-frequency conductive line 35 extends into the liquid feed passage 31 and transmits a high-frequency current from the proximal side to the distal side in the instrument body 2h. That is, the high-frequency conductive line 35 transmits the high-frequency current from the power source 4 to the electrode 24.

By this, the electrode 24 discharges the high-frequency current having transmitted through the high-frequency conductive line 35 along the mist-state liquid W atomized from a liquid atomizing port 24k, which will be described later, so as to coagulate the surface layer of a living tissue.

The transducer 32 imparts ultrasonic vibration to the liquid W flowing through the liquid feed passage 31 and includes a Langevin type transducer or a magnetostrictive transducer. At the distal end and the proximal end of the transducer 32, an insulating plate 38 for preventing malfunction of the transducer 32 due to intrusion of the high-frequency current into the ultrasonic driving system is disposed.

Moreover, the liquid feed passage 31 is formed inside the tube 23 and inside the transducer 32, the horn 33 and the electrode 24. An opening at the distal side of the liquid feed passage 31 formed inside the electrode 24 constitutes the liquid atomizing port 24k. The liquid atomizing port 24k is to inject the liquid W, which is given ultrasonic vibration by the transducer 32 and atomized, in the mist state from the distal end of the instrument body 2h to the living tissue.

Also, at the proximal side of the transducer 32, the other end of an ultrasonic signal line 36, which is a lead wire, having one end connected to the plug 21 is connected. The ultrasonic signal line 36 transmits a current for ultrasonic driving from the proximal side to the distal side in the instrument body 2h. That is, the ultrasonic signal line 36 transmits the current for ultrasonic driving from the power source 4 to the transducer 32.

As shown in FIG. 4, one end of the high-frequency conductive line 35 is connected to a high-frequency plug body 41 connected to the plug 21 in the cable connection portion 20, and one end of the ultrasonic signal line 36 is connected to an ultrasonic plug body 43 connected to the plug 21 in the cable connection portion 20.

Next, operation of this so constructed embodiment will be described.

First, the liquid feed pump 6 is driven to start liquid feed, the liquid W flows from the liquid feed container 7 through the liquid feed tube 8 and from the connector 22 for liquid feed tube into the liquid feed passage 31.

Substantially at the same time, by input of the foot switch 5, a current for ultrasonic driving from the power source 4 is supplied through the conductive cable 9, the plug 21, the ultrasonic plug body 43 and the ultrasonic signal line 36 to the transducer 32, and a high-frequency current from the power source 4 is supplied through the conductive cable 9, the plug 21, the high-frequency plug body 41 and the high-frequency conductive line 35 to the electrode 24.

It is to be noted that the liquid feed pump 6 and the power source 4 are connected to each other by a communication cable so that the liquid feed pump 6 can be controlled from the power source 4.

After that, when the transducer 32 is vibrated by supply of the current for ultrasonic driving, the liquid W flowing through the liquid feed passage 31 is given ultrasonic vibration, and as a result, the atomized liquid W is injected to the target tissue in the mist state from the fluid atomizing port 24k at the distal end of the instrument body 2h.

Substantially at the same time, the electrode 24 discharges the high-frequency current along the liquid W injected in the mist state from the fluid atomizing port 24k.

In this way, according to the construction and operation of this embodiment, since the electrode 24 discharges the high-frequency current along the liquid W injected in the mist state from the fluid atomizing port 24k, the target tissue can be coagulated without bringing the treatment portion 26 into contact with the target tissue.

Also, by atomizing the liquid W using the ultrasonic vibration of the transducer 32, a liquid amount to be supplied to the target tissue becomes lower than conventional liquid amount, and since the atomization with a small particle diameter can be injected to the target tissue, favorable discharge with high coagulation force can be performed for the target tissue from the electrode 24.

As a result, since favorable discharge can be obtained, which prolongs the discharge distance between the electrode 24 and the target tissue, operability of the treatment instrument 2 is improved.

From the above, since an injection amount of a liquid to be injected to the target tissue can be reduced with a simple construction and moreover, since atomization of a liquid with smaller particle diameter is generated, a treatment instrument with improved coagulability for the target tissue can be provided.

Second Embodiment

Figure 5:
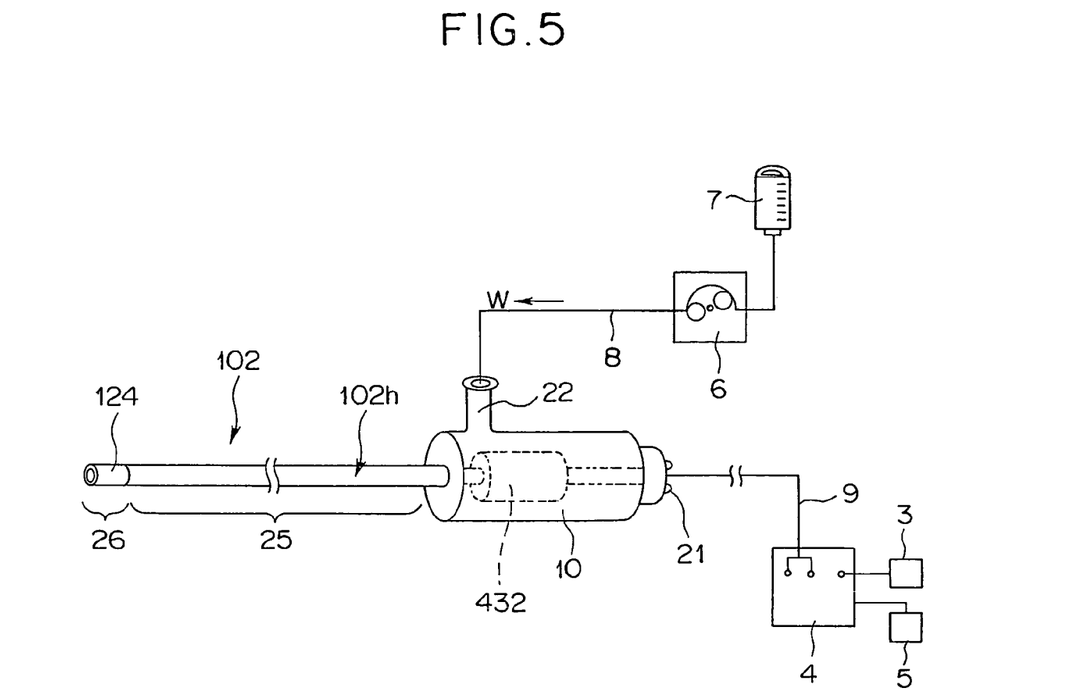
FIG. 5 is a block diagram showing a treatment instrument system provided with a treatment instrument showing a second embodiment.
Figure 6:
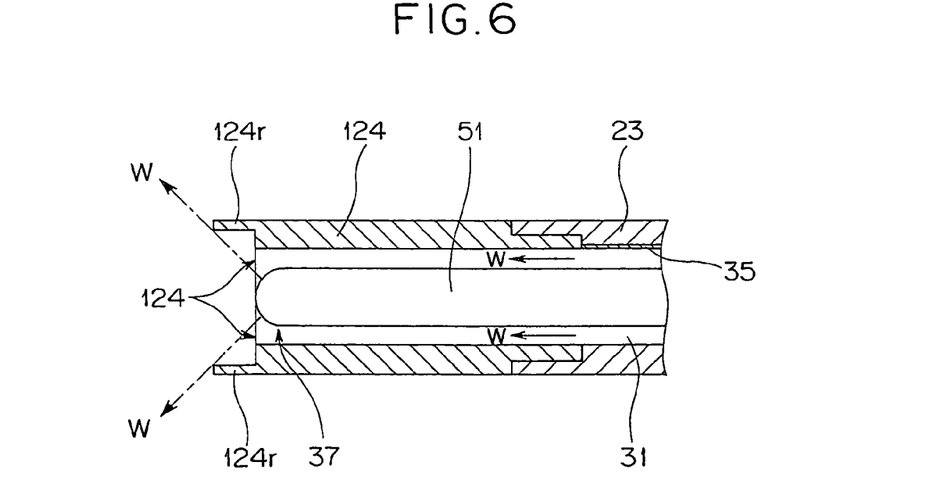
FIG. 6 is a partial sectional view of the distal side of the treatment instrument in FIG. 5.

FIG. 5 is a block diagram showing a treatment instrument system provided with a treatment instrument showing this embodiment, and FIG. 6 is a partial sectional view of the distal side of the treatment instrument in FIG. 5.

The construction of the treatment instrument of this embodiment is different from the treatment instrument of the first embodiment shown in FIGS. 1 to 4 in the point that the transducer is built in the proximal side of the treatment instrument and the electrode is fixed to the distal end of the tube. Thus, only the difference will be described and the same reference numerals are given to the same construction as those in the first embodiment, and the description will be omitted.

As shown in FIG. 5, a treatment instrument 102 is provided with an instrument body 102h. A transducer 432 is provided inside the proximal portion 10 of the instrument body 102h. The transducer 432 corresponds to the transducer 32 of the first embodiment.

Also, as shown in FIG. 6, a tubular electrode 124 is connected to the distal end of the tube 23 of the insertion portion 25 of the instrument body 102h. The electrode 124 corresponds to the electrode 24 of the first embodiment.

In this embodiment, too, the tube 23 and the proximal portion 10 constitute a cylindrical member in the present invention.

At the distal end of the electrode 124, a ring-shaped distal portion 124r which is thinner than the electrode 124 is provided. The distal portion 124r is located protruding from the distal end of a vibration probe 51, which will be described later, toward the distal side.

In this embodiment, too, the other end of the high-frequency conductive line 35 having one end connected to the plug 21 is connected to the proximal end of the electrode 124.

In bores of the tube 23 and the electrode 124, the vibration probe 51, which is an elongated flexible ultrasonic probe connected to a transducer 432 is disposed along the bores. The distal portion of the vibration probe 51 constitutes a mist generation portion 37.

Moreover, in a space between the vibration probe 51 and the inside of the tube 23, a liquid feed passage 31, which is a liquid channel through which the liquid W passes is formed from the proximal side to the distal side of the instrument body 102h. An opening at the distal side of the instrument body 102h of the liquid feed passage 31 constitutes the liquid atomizing port 124k. In addition, the liquid atomizing port 124k is located on the proximal side away from the distal portion 124r.

Next, action of the treatment instrument of this embodiment constituted as above will be described.

At the same time that the liquid W is fed through the liquid feed passage 31 to the vicinity of the mist generation portion 37 of the vibration probe 51, the transducer 432 is ultrasonic-vibrated, and the ultrasonic vibration is transmitted to the vibration probe 51, whereby the liquid W to which the ultrasonic vibration is applied by the vibration probe 51 is atomized in the vicinity of the mist generation portion 37. After that, the atomized liquid W is injected in the mist state from the liquid atomizing port 124k.

Also, substantially at the same time, the high-frequency current is discharged from the distal portion 124r of the electrode 124 along the mist-state liquid W.

According to the above construction and action, since the transducer 432 is provided at the proximal portion 10, the size of the transducer 432 can be increased as compared with the first embodiment. Therefore, there are more options for the frequency or amplitude of the vibration of the transducer 432 and adjustment of the atomization particle diameter and atomizing form suitable for discharge is facilitated, by which favorable coagulation for the target tissue can be obtained.

Moreover, by forming the ring-shaped distal portion 124r, the inner diameter of the distal portion 124r can be made larger than the inner diameter of the electrode 24 of the first embodiment, by which the injection range at one time can be increased. It should be noted that the other effects are the same as those of the above-mentioned first embodiment.

Third Embodiment

Figure 7:
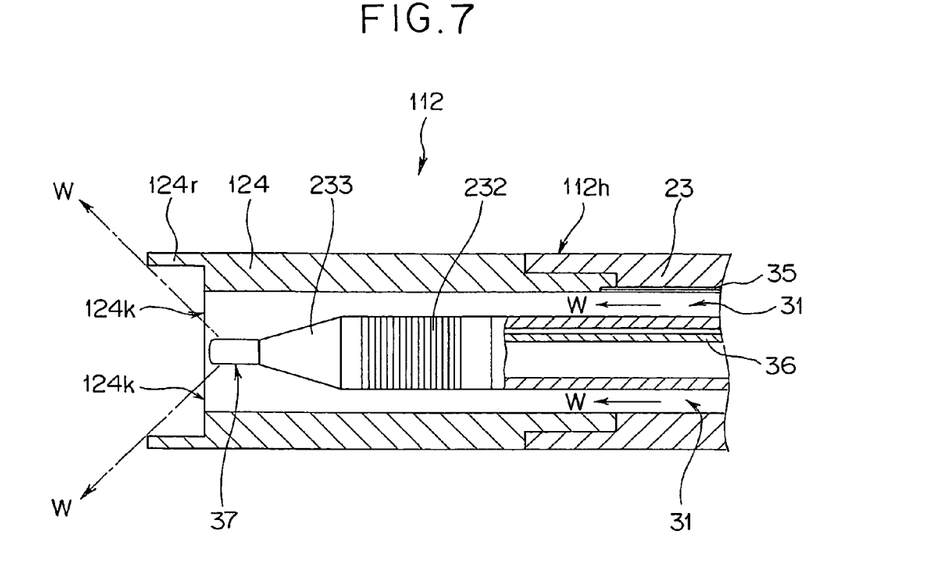
FIG. 7 is a partial sectional view of the distal side of a treatment instrument showing a third embodiment.

FIG. 7 is a partial sectional view of the distal side of the treatment instrument showing this embodiment. The construction of the treatment instrument of this embodiment is different from that in the second embodiment shown in FIGS. 5 and 6 in the point that the rod-shaped transducer is disposed at the distal side of the treatment instrument. Thus, only this difference will be described, and the same reference numerals are given to the same construction as those in the second embodiment and the description will be omitted.

As shown in FIG. 7, inside the tube 23 and the electrode 124 of the treatment instrument 112, a rod-shaped transducer 232 of the Langevin (electrostrictive) type for generating ultrasonic vibration is provided, and a conical horn 233 for amplifying the amplitude is provided at the distal side of the transducer 232.

The transducer 232 and the horn 233 correspond to the transducer 32 and the horn 33 respectively in the first embodiment. Also, the distal side of the horn 233 constitutes the mist generation portion 37.

In a space between the transducer 232 as well as the horn 233 and the tube 23 as well as the electrode 124, the liquid feed passage 31, which is a liquid channel, is formed. Also, the ultrasonic signal line 36 having one end connected to the plug 21 and the other end to the transducer 232 is extended to the liquid feed passage 31.

An opening at the distal side of the instrument body 112h of the liquid feed passage 31 constitutes the liquid atomizing port 124k. Also, the liquid atomizing port 124k is located on the distal side away from the distal portion 124r.

In this embodiment, too, the tube 23 and the proximal portion 10 constitute the cylindrical member in the present invention.

Next, operation of the embodiment constructed as above will be described.

First, when the transducer 232 is ultrasonic-vibrated at the same time that the liquid W is fed by the liquid feed passage 31 to the vicinity of the mist generation portion 37, the ultrasonic vibration is applied to the liquid W, the liquid W is atomized, and atomization is generated at the mist generation portion 37. As a result, the liquid W is injected from the liquid atomizing port 124k in the mist state.

At injection of the liquid W, the high-frequency current from the high-frequency power source is conducted through the distal portion 124r, and electric discharge is performed for the target tissue along the injection of the liquid W.

According to the construction and operation as mentioned above, since the transducer 232 is located on the distal portion side of the treatment instrument 112 as compared with the above-mentioned second embodiment, loss of the generated ultrasonic vibration can be reduced more than in the second embodiment, and the liquid W can be injected efficiently. The other effects are the same as those of the above-mentioned second embodiment.

Fourth Embodiment

Figure 8:
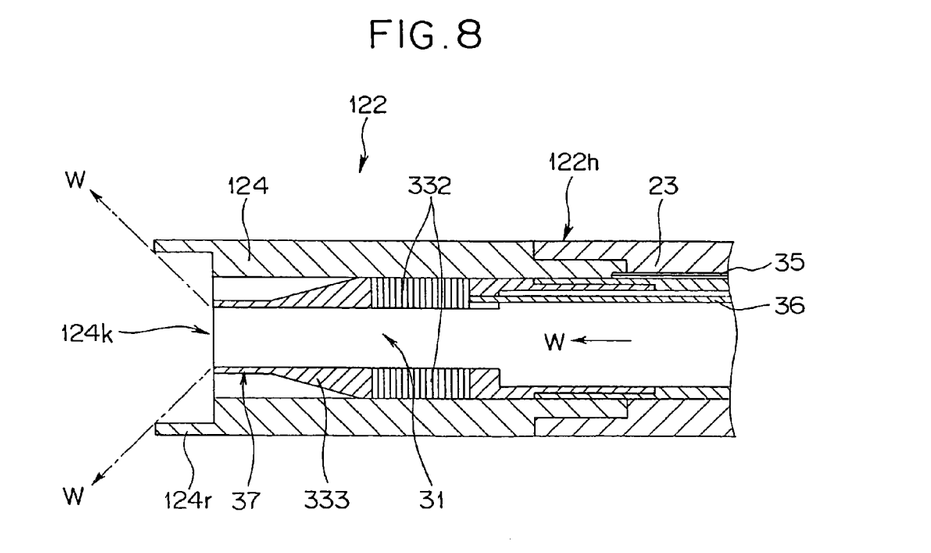
FIG. 8 is a partial sectional view of the distal side of a treatment instrument showing a fourth embodiment.

FIG. 8 is a partial sectional view of the distal side of the treatment instrument showing this embodiment. The construction of the treatment instrument of this embodiment is different from the treatment instrument of the third embodiment shown in FIG. 7 in the point that the transducer is formed in the tubular shape. Thus, only this difference will be described, and the same reference numerals are given to the same construction as those in the third embodiment, and the description will be omitted.

As shown in FIG. 8, inside the tube 23 and the electrode 124 of the treatment instrument 122, a tubular transducer 332 for generating ultrasonic vibration is provided, and a conical tubular horn 333 for amplifying the amplitude is provided at the distal side of the transducer 332. It should be noted that the transducer 332 and the horn 333 correspond to the transducer 32 and the horn 33 respectively of the first embodiment. Also, the distal side of the horn 333 constitutes the mist generation portion 37.

Moreover, in a space inside the transducer 332 and the horn 333, the liquid feed passage 31, which is a fluid channel, is formed.

An opening at the distal side of the instrument body 122h of the liquid feed passage 31 constitutes the liquid atomizing port 124k. Also, the liquid atomizing port 124k is located on the proximal side away from the distal portion 124r.

In this embodiment, too, the tube 23 and the proximal portion 10 constitute the cylindrical member in the present invention.

According to the construction of this embodiment, since the liquid W is fed into the transducer 332 through the internal space, the liquid W can be supplied to the mist generation portion 37 more stably than in the third embodiment. It should be noted that the other effects are the same as those of the above-mentioned third embodiment.

Figure 9:
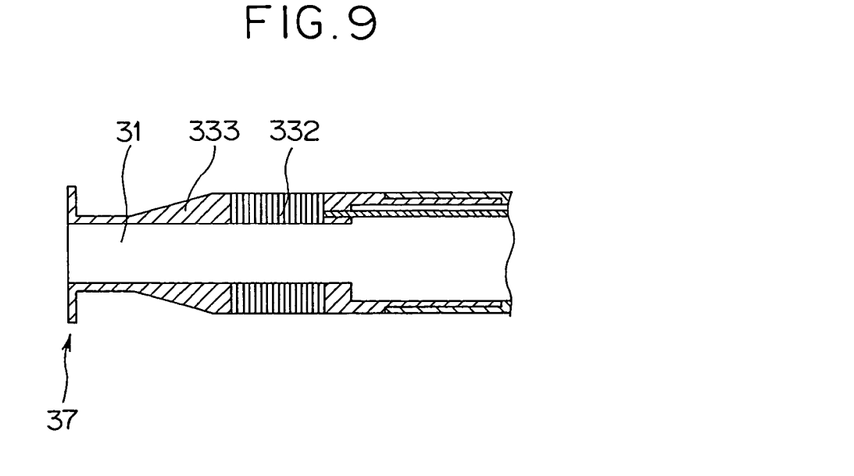
FIG. 9 is a partial sectional view showing a variation of the shape of a horn in FIG. 8.
Figure 10:
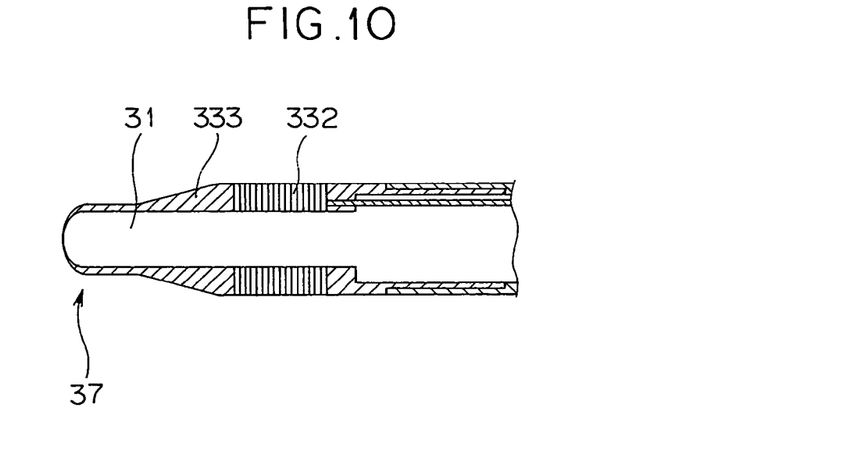
FIG. 10 is a partial sectional view showing another variation of the shape of a horn in FIG. 8.
Figure 11:
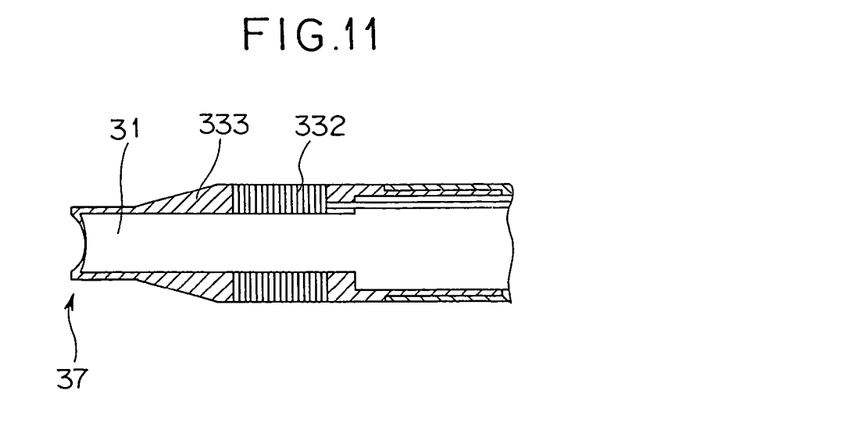
FIG. 11 is a partial sectional view showing still another variation of the shape of a horn in FIG. 8.

FIG. 9 is a partial sectional view showing a variation of the shape of the horn in FIG. 8, FIG. 10 is a partial sectional view showing another variation of the shape of the horn in FIG. 8, and FIG. 11 is a partial sectional view showing still another variation of the shape of the horn in FIG. 8.

In the above-mentioned embodiment, the shape of the distal end of the horn 333 is formed in the end-face shape as shown in FIG. 8, but not limited to this, it may be the T-shape as shown in FIG. 9, a projecting shape having the R shape as shown in FIG. 10 or a recessed shape having the R shape as shown in FIG. 11.

By changing the shape of the distal portion of the horn 333 in this way, the atomizing form of the liquid W injected from the liquid atomizing port 124k is changed, and the optimal atomizing form for coagulability of the target tissue can be selected.

Fifth Embodiment

Figure 12:
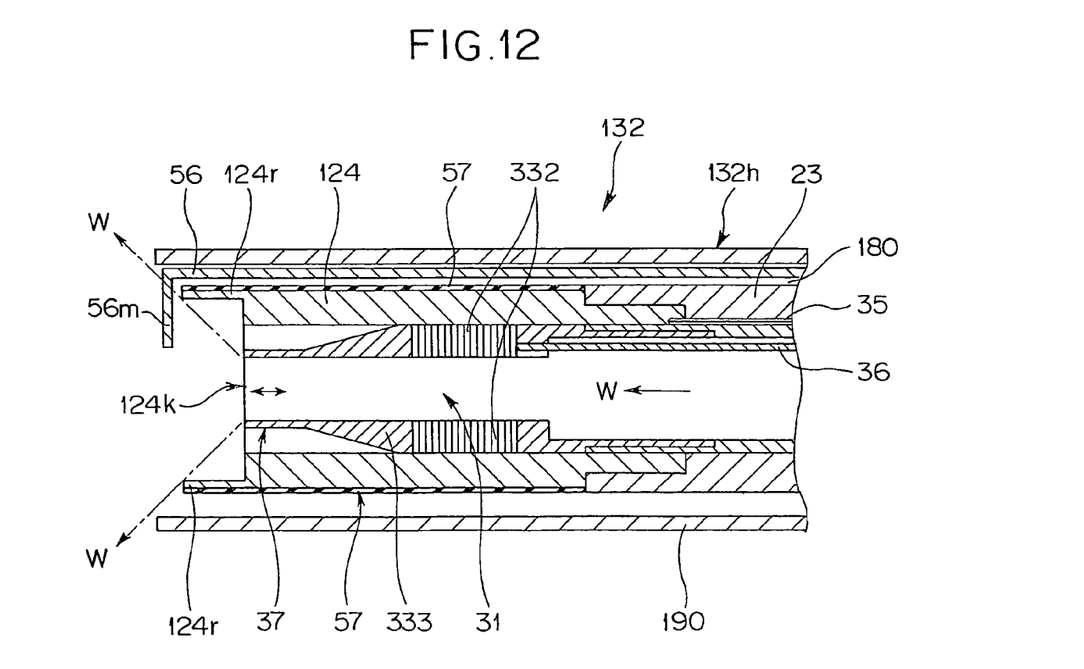
FIG. 12 is a partial sectional view of the distal side of a treatment instrument showing a fifth embodiment.

FIG. 12 is a partial sectional view of the distal side of the treatment instrument showing this embodiment. The construction of the treatment instrument of this embodiment is different from the treatment instrument in the fourth embodiment shown in FIG. 8 in the point that the outside of the instrument body is coated by a protective tube. Thus, only this difference will be described and the same reference numerals are given to the same construction as those in the fourth embodiment, and the description will be omitted.

As shown in FIG. 12, in an instrument body 132h of a treatment instrument 132, the outside of the tube 23 and the electrode 124 are covered by a protective tube 190 so that a space 180 is provided between the protective tube and the outside of the tube 23 and the electrode 124. In this embodiment, too, the tube 23 and the proximal portion 10 constitute the cylindrical member in the present invention.

Also, in the space 180, an elongated rod-shaped electrode 56 is disposed. The electrode 56 includes a conductive rod-shaped member in the L shape having a portion of 56m bent at a position overlapping with the liquid W injected from the atomizing port 124k in the plane at the distal portion of the instrument body 132h.

In addition, the electrode 56 is capable of moving forward/backward the distal side and the proximal side of the instrument body 132h in the space 180. Moreover, to the electrode 56, the high-frequency plug body 41 (See FIG. 4) is connected.

On the outside of the electrode 124, an insulating layer 57 for electrically insulating the electrode 124 from the electrode 56 is formed.

Next, operation of the so constructed embodiment will be described. Since the operation of the electrode 124 and the operation of the transducer 332 are the same as in the fourth embodiment, the description will be omitted.

After the electrode 56 is protruded to the distal side away from the distal portion 124r of the electrode 124 in the state where the liquid W is not atomized, the high-frequency current is conducted from the power source 4. After that, the portion 56m is brought into contact with the target tissue and the high-frequency current is directly supplied from the portion 56m, whereby dissection or spot hemostatic cautery is performed at the target tissue.

According to the construction and action of this embodiment, both coagulation of the surface layer portion of the target tissue and dissection of the tissue can be performed by a single treatment instrument using the electrode 124 and the electrode 56 in this way. It should be noted that the other effects are the same as those of the above-mentioned fourth embodiment.

Sixth Embodiment

Figure 13:
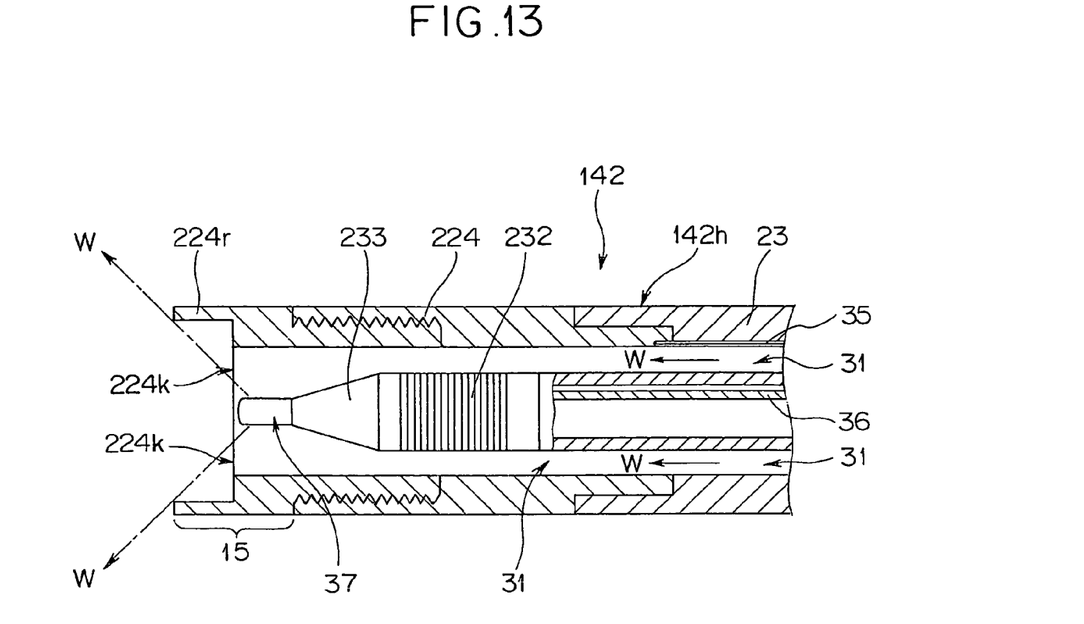
FIG. 13 is partial sectional view of the distal side of a treatment instrument showing a sixth embodiment.

FIG. 13 is a partial sectional view of the distal side of the treatment instrument of this embodiment. The construction of the treatment instrument of this embodiment is different from the treatment instrument in the third embodiment shown in FIG. 7 in the point that the distal side of the electrode can be freely removed. Thus, only this difference will be described and the same reference numerals are given to the same construction as those in the fifth embodiment, and the description will be omitted.

As shown in FIG. 13, an electrode 224 on the distal side of an instrument body 142h of a treatment instrument 142 includes a tubular member, and at the distal side of the electrode 224, a disposable electrode 15 provided with a distal portion 224r is formed.

The electrode 224 corresponds to the electrode 124 in the third embodiment. Also, the disposable electrode 15 is removable with respect to the distal side of the electrode 224. Moreover, an opening on the distal side of the liquid feed passage 31 of the electrode 224 constitutes the liquid atomizing port 224k.

Also, in this embodiment, the high-frequency current is discharged from the disposable electrode 15 along the liquid W injected in the mist state. In this embodiment, too, the tube 23 and the proximal portion 10 constitute the cylindrical member in the present invention.

According to such a construction, since it is necessary to replace only the distal portion of the electrode 224, that is, the disposable electrode 15 when replacing the electrode 224 which is worn by discharge, and running costs of the treatment instrument can be reduced.

Seventh Embodiment

Figure 14:
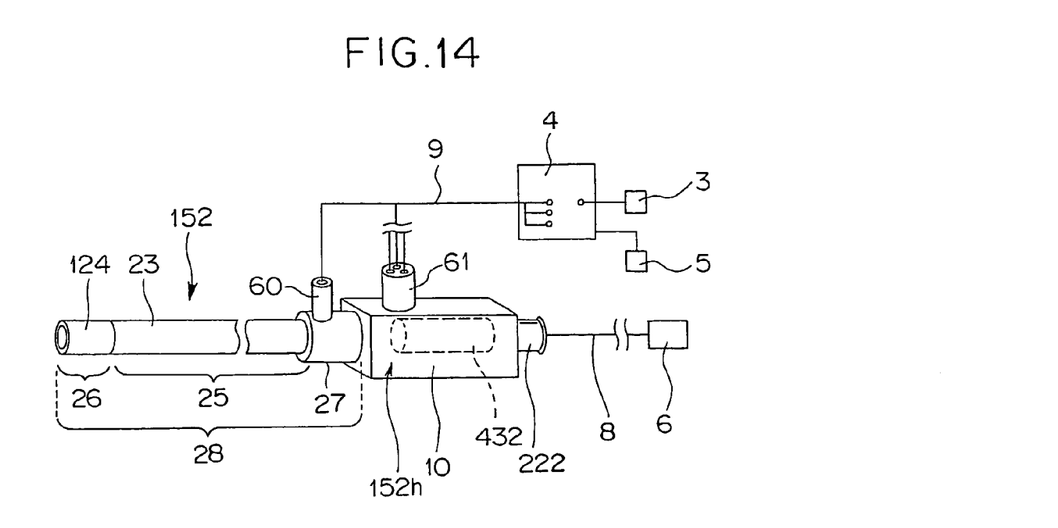
FIG. 14 is a block diagram showing a treatment instrument system provided with a treatment instrument showing a seventh embodiment.
Figure 15:
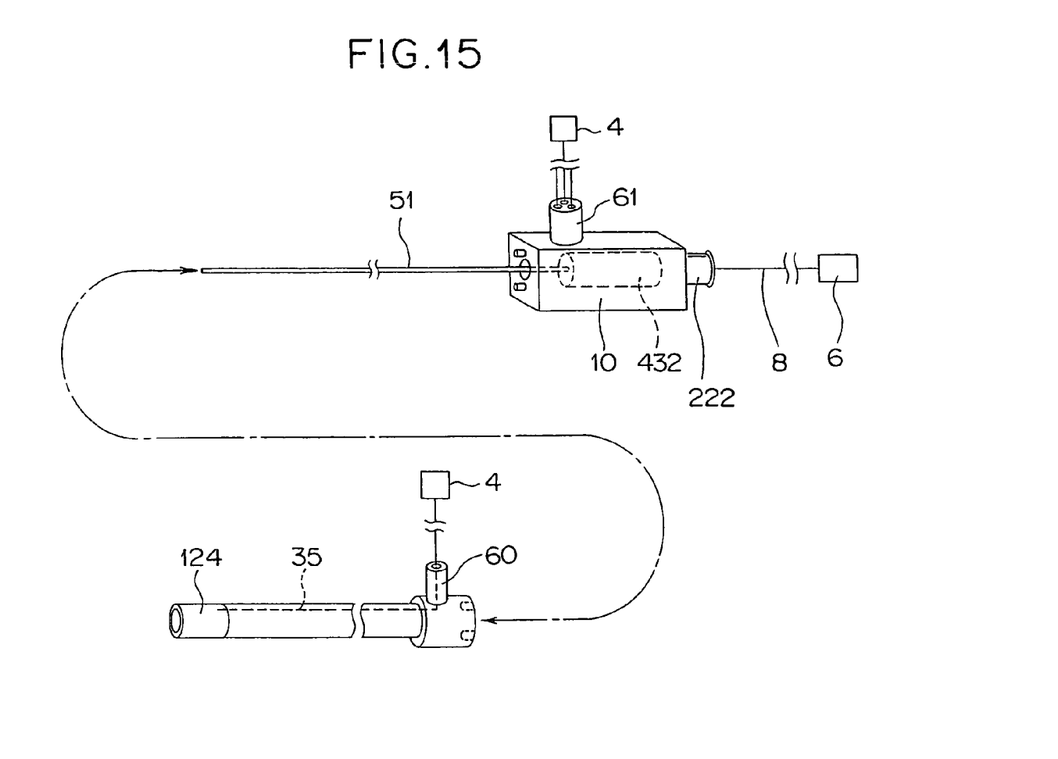
FIG. 15 is an exploded perspective view of the treatment instrument showing a state where a disposable portion of the treatment instrument in FIG. 14 is removed from the proximal portion.

FIG. 14 is a block diagram showing a treatment instrument system provided with a treatment instrument showing this embodiment, and FIG. 15 is an exploded perspective view of the treatment instrument showing a state where the disposable portion of the treatment instrument in FIG. 14 is removed from the proximal portion.

The construction of the treatment instrument of this embodiment is different from the treatment instrument in the second embodiment shown in FIG. 5 in the point that the portion including the insertion portion of the treatment instrument can be removed from the proximal portion. Thus, only this difference will be described and the same reference numerals are given to the same construction as those in the second embodiment, and the description will be omitted.

As shown in FIG. 14, a disposable portion 28, which is a removable member of an instrument body 152h of a treatment instrument 152 mainly includes the treatment portion 26 on which the electrode 124 is formed, the insertion portion 25 and a disposable portion connection portion 27 consecutively formed from the distal side.

At the disposable portion connection portion 27, a connector 60 for high-frequency conductive line connection is disposed. Also, at the proximal portion 10 on which the transducer 432 is disposed, a connector 61 for ultrasonic signal line connection is disposed. Moreover, the connector 60 for high-frequency conductive line connection and the connector 61 for ultrasonic signal line connection are connected to the conductive cable 9, respectively.

As shown in FIG. 15, the disposable portion 28 is capable of removal from the proximal portion 10 at the disposable portion connection portion 27.

Moreover, the disposable portion 28 has a high-frequency conductive line 35 incorporated in the liquid feed passage 31 from the connector 60 for high-frequency conductive line connection to the treatment portion 26.

Furthermore, a connector 222 for liquid feed tube, which is a connector for liquid feed corresponding to the above-mentioned connector 22 for liquid feed tube, is provided at the proximal portion 10. Thus, to the connector 222 for liquid feed tube, too, as mentioned above, one end of the liquid feed tube 8 with the liquid feed pump 6 interposed at the middle position is connected.

In this embodiment, too, the tube 23 and the proximal portion 10 constitute the cylindrical member in the present invention.

Next, action of the so constructed embodiment will be described.

First, when the treatment instrument 152 is to be used, the disposable portion 28 is used in the state where it is connected to the proximal portion 10 through the disposable portion connection portion 27. The current for ultrasonic driving is supplied to the transducer 432 in the proximal portion 10 from the conductive cable 9 through the connector 61 for ultrasonic signal line connection.

As a result, the ultrasonic vibration generated at the transducer 432 is transmitted to the vibration probe 51, and the liquid W fed from the liquid feed passage 31 is atomized into the mist state at the distal portion of the vibration probe 51.

Also, after the high-frequency current is supplied from the conductive cable 9 through the connector 60 for wire connection and the high-frequency conductive line 35 incorporated in the disposable portion 28 to the electrode 124 of the treatment portion 26, the high-frequency current is discharged along the liquid W injected in the mist state at the electrode 124.

Then, if the electrode 124 is worn after the treatment instrument 152 is used several times, the disposable portion 28 is removed from the proximal portion 10 through the disposable portion connection portion 27 so as to replace the disposable portion 28.

According to the construction and action of this embodiment, by replacing the disposable portion 28, the electrode 124 which is worn by electric discharge can be easily replaced. The other effects are the same as those of the above-mentioned second embodiment.

Figure 16:
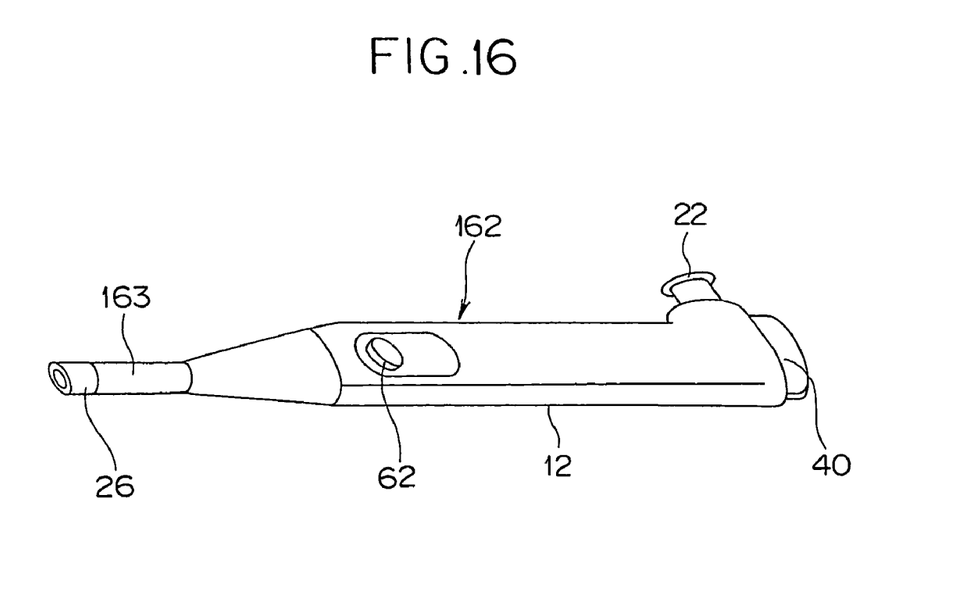
FIG. 16 is a perspective view showing a handpiece for an abdominal surgery.

The treatment instruments described in the first to the seventh embodiments include a handpiece for an abdominal surgery, for example. FIG. 16 is a perspective view showing the handpiece for an abdominal surgery.

As shown in FIG. 16, a handpiece 162 has a handpiece portion 12, and at the distal side of the handpiece portion 12, the treatment portion 26 is provided through a rigid tubular member 163.

At the handpiece portion 12, a hand switch 62 for controlling high-frequency electric energy, the liquid feed connector 22 and the cable connector 40 are provided.

In this way, when the treatment instrument in the above-mentioned first to the seventh embodiments is applied to the handpiece, a user holds the handpiece portion 12 and performs electric discharge while atomizing the liquid W from the treatment portion 26 for coagulation procedure for the target tissue.

According to this, when applied to the handpiece 162, since the handpiece portion 12 and the treatment portion 26 are close to each other, it has an advantage of suitability for a treatment of an abdominal surgery when the target tissue is close to the handpiece 162.

Figure 17:
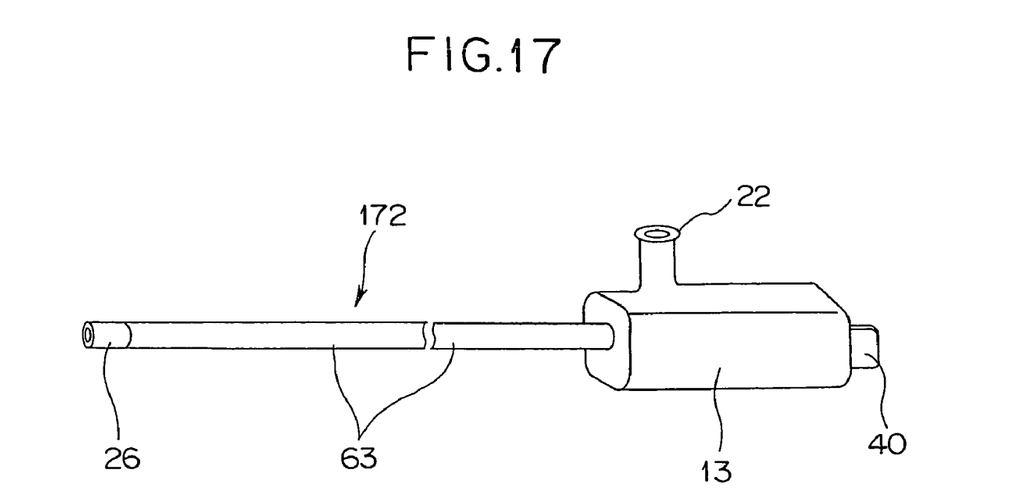
FIG. 17 is a perspective view showing a treatment instrument during laparoscopy.

Alternatively, the treatment instruments described in the first to the seventh embodiments include a treatment instrument for a surgery under laparoscope, for example. FIG. 17 is a perspective view showing the treatment instrument for a surgery under laparoscope.

As shown in FIG. 17, a treatment instrument 172 has a handle portion 13, and at the distal side of the handle portion 13, an insertion portion 63 which can be inserted into a trocar and includes a rigid shaft is provided. Also, at the distal end of the insertion portion 63, the treatment portion 26 is constructed.

When the treatment instrument of the above-mentioned first to the seventh embodiments is applied to a treatment instrument for surgery under laparoscope in this way, the user holds the handle portion 13, inserts the insertion portion 63 into the trocar, and performs electric discharge while atomizing the liquid from the treatment portion 26 under a laparoscope for coagulation procedure.

According to this, when applied to the treatment instrument 172 for surgery under laparoscope, since a rigid shaft is provided, it has an advantage that suitability for treatment under laparoscope can be obtained.

It is needless to say that the above-mentioned first to the seventh embodiments may be applied to other electrosurgical instruments using both the high-frequency electric energy and the conductive fluid for coagulating the surface layer of a living tissue by electric discharge along the conductive fluid.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An electrosurgical instrument comprising:
   an elongated instrument body;
   a cylindrical member constituting the instrument body;
   an ultrasonic transducer provided at a proximal side of the instrument body and inside of the cylindrical member;

an ultrasonic probe for applying an ultrasonic vibration of the ultrasonic transducer to a conductive fluid flowing into the inside of the cylindrical member at a distal side of the elongated instrument body, the ultrasonic probe being connected to the ultrasonic transducer and extending to a distal end of the instrument body in the inside of the cylindrical member;

a fluid atomizing port provided at the distal side of the instrument body for injecting to a living tissue from the distal end of the instrument body the conductive fluid which was given the ultrasonic vibration by the ultrasonic probe and atomized; and an electrode provided at the distal side of the instrument body for discharging high-frequency electric energy along the conductive fluid atomized from the fluid atomizing port.

2. The electrosurgical instrument according to claim 1, wherein the electrode is provided at the distal end of the instrument body.

* * * * *